United States Patent
Saffie-Siebert et al.

(10) Patent No.: US 10,967,171 B2
(45) Date of Patent: Apr. 6, 2021

(54) APPARATUS AND METHODS FOR THE TRANSDERMAL DELIVERY OF ACTIVE AGENTS

(71) Applicant: SISAF LTD., Surrey (GB)

(72) Inventors: Roghieh Suzanne Saffie-Siebert, Surrey (GB); Christopher Burns, Surrey (GB)

(73) Assignee: SISAF LTD., Surrey (GB)

( * ) Notice: Subject to any disclaimer, the term of this patent is extended or adjusted under 35 U.S.C. 154(b) by 0 days.

(21) Appl. No.: 16/652,843

(22) PCT Filed: Nov. 9, 2018

(86) PCT No.: PCT/GB2018/053252
§ 371 (c)(1),
(2) Date: Apr. 1, 2020

(87) PCT Pub. No.: WO2019/092436
PCT Pub. Date: May 16, 2019

(65) Prior Publication Data
US 2020/0230395 A1    Jul. 23, 2020

(30) Foreign Application Priority Data
Nov. 10, 2017   (GB) ..................................... 1718636

(51) Int. Cl.
*A61N 1/04*       (2006.01)
*A61N 1/30*       (2006.01)
(Continued)

(52) U.S. Cl.
CPC ....... *A61N 1/0412* (2013.01); *A61M 37/0015* (2013.01); *A61N 1/0432* (2013.01);
(Continued)

(58) Field of Classification Search
None
See application file for complete search history.

(56) References Cited

U.S. PATENT DOCUMENTS 4,969,468 A * 11/1990 Byers .................. A61B 5/0422
                                                    29/829
6,009,345 A    12/1999 Hofmann
(Continued)

FOREIGN PATENT DOCUMENTS

EP        2 737 923 A2     6/2014
JP        2015-173901 A1  10/2015
(Continued)

OTHER PUBLICATIONS

International Search Report issued in International Application No. PCT/GB2018/053252, dated Jan. 3, 2019.
(Continued)

*Primary Examiner* — Nathan R Price
*Assistant Examiner* — Weng Lee
(74) *Attorney, Agent, or Firm* — Charles C. Achkar; Ostrolenk Faber LLP.

(57) ABSTRACT

A transdermal delivery system (1) configured to deliver an active agent to human or animal tissue, comprising a penetrative electrode (2) of one polarity that provides an electrical contact (3) beneath the stratum corneum (20); a surface electrode (4) of the opposite polarisation to that of the penetrative electrode (2) that provides an electrical contact to the external surface of the skin (21) on the opposite side of the stratum corneum (20) to the electrical contact (3) of the penetrative electrode (2); a dispenser (5) configured to deliver of an active agent to the external surface of the skin (21) adjacent to an electrical contact of the surface electrode (4); a method of delivering the active agent to the tissue of a human or animal body using the
(Continued)

transdermal delivery system (1) and an electrode assembly (10) for use in preparing the transdermal delivery system (1).

16 Claims, 4 Drawing Sheets

(51) Int. Cl.
  *A61N 1/40* (2006.01)
  *A61M 37/00* (2006.01)
  *A61K 9/00* (2006.01)

(52) U.S. Cl.
  CPC ........... *A61N 1/0476* (2013.01); *A61N 1/303* (2013.01); *A61N 1/306* (2013.01); *A61N 1/40* (2013.01); *A61K 9/0021* (2013.01); *A61M 2037/0023* (2013.01); *A61N 1/0444* (2013.01); *A61N 1/0448* (2013.01)

(56) References Cited

U.S. PATENT DOCUMENTS

| | | | |
|---|---|---|---|
| 6,503,231 | B1 | 1/2003 | Prausnitz et al. |
| 6,591,133 | B1 | 7/2003 | Joshi |
| 6,918,901 | B1 * | 7/2005 | Theeuwes ............ A61B 17/205 |
| | | | 600/309 |
| 2002/0198512 | A1 | 12/2002 | Seward |
| 2005/0273046 | A1 * | 12/2005 | Kwiatkowski ......... A61N 1/325 |
| | | | 604/20 |
| 2007/0078376 | A1 | 4/2007 | Smith |
| 2007/0142885 | A1 * | 6/2007 | Hantash ................... A61N 1/06 |
| | | | 607/102 |
| 2010/0274327 | A1 | 10/2010 | Carroll et al. |
| 2014/0142492 | A1 | 5/2014 | Jung et al. |

FOREIGN PATENT DOCUMENTS

| | | |
|---|---|---|
| TW | 201639546 A | 11/2016 |
| WO | WO 2007/030415 | 3/2007 |
| WO | WO 2014/193725 A1 | 12/2014 |
| WO | WO 2014/201511 A1 | 12/2014 |
| WO | WO2016/205895 A1 | 12/2016 |
| WO | WO2017/014091 A1 | 1/2017 |

OTHER PUBLICATIONS

Written Opinion of the International Searching Authority issued in International Application No. PCT/GB2018/053252, dated Jan. 3, 2019.
Search Report issued in GB 1718636.2, dated Apr. 19, 2018.
International Preliminary Report on Patentability (Chapter II of the Patent Cooperation Treaty) issued in International Application No. PCT/GB2018/053252, dated Oct. 31, 2019.
Advanced Drug Delivery Reviews 35 (1999) 21-39; Theory of Elelectrical creation of aqueous pathways across skin transport barriers.
Pharmaceutics 2015, 7, 438-470; Transdermal Drug Delivery: Innovative Pharmaceutical Developments Based on Disruption of the Barrier Properties of the stratum corneum.

* cited by examiner

APPARATUS AND METHODS FOR THE TRANSDERMAL DELIVERY OF ACTIVE AGENTS

CROSS-REFERENCE TO RELATED APPLICATIONS

The present application is a § 371 National Phase application based on PCT/GB2018/053252 filed Nov. 9, 2018, which claims the benefit Great Britain Appl. No. 1718636.2, filed Nov. 10, 2017, the subject matter of which is hereby incorporated in its entirety.

FIELD OF THE INVENTION

The present invention concerns transdermal delivery of active agents. More particularly, but not exclusively, this invention concerns apparatus for transdermal delivery of active agents e.g. by electroporation and/or iontophoresis. The invention also concerns a method for transdermal delivery of active agents, e.g. by electroporation and/or iontophoresis.

BACKGROUND OF THE INVENTION

The outer layer of the skin of a human is the stratum corneum protective barrier that protects the body against harmful contaminations found in the environment and at the same time regulates the moisture levels below the skin preventing the body from drying out and helping healthy cell growth. This stratum corneum has often been described by the "brick wall" analogy where the skin cells or corneocytes can be seen as the bricks and the fat or lipids acting as the mortar. This 10-15 µm protective layer makes it very difficult for anything to pass through.

There have been various ways developed to pass the stratum corneum such as using active or passive methods such as chemical additives, transdermal needles, micro needles, skin ablation or burning, iontophoresis, electroporation, ultrasound. A more detailed description can be found in Pharmaceutics, 2015, 7, 438-470; *Transdermal Drug Delivery: Innovative Pharmaceutical Developments Based on Disruption of the Barrier Properties of the stratum corneum.*

Conventional iontophoresis devices include a positive electrode and a negative electrode positioned on the surface of the skin. By using electromotive repulsion between the electrical field and the pharmaceutical compounds, the pharmaceutical compound is delivered to a blood vessel deeper in the stratum. Another iontophoretic delivery system comprises their electrodes having two sets of metallic film for applying a pulsed voltages to a patch to increase drug-penetration capabilities.

Electroporation is a technique used where an electrical field is applied to cells in order to increase the permeability of the cell membrane, thereby allowing active ingredients such as chemicals, drugs or DNA to be introduced into the cell. The principle is that an electric field generated by a high voltage pulse between two electrodes causes a transient dielectric breakdown of the plasma membrane of cells within the high intensity electric field. As a result pores open between the skin cells. Conventional electroporation uses electric fields between physically separated electrodes resulting in a direct current path through the plain of the skin tissue between the electrodes.

JP2015-173901 describes a transdermal delivery device which comprises an array of microneedles, a drug carrier layer that contacts the needle-free surface of the array, a DC circuit and an AC circuit. This device enables charged drug molecules to be transported across the stratum corneum in response to an applied electric field. In the device of JP2015-173901, each microneedle is entirely coated with a conducting layer and thus provides an electrode that extends across the stratum corneum. There is no disclosure of a microneedle comprising a shaft with an insulated exterior and a conducting tip or any other arrangement of electrically isolated electrodes disposed on either side of the stratum corneum such that an electric field can be applied across the stratum corneum.

WO2016/205895 describes an electroporation system comprising an electroporation probe have at least two contiguous electrodes configured to be inserted into biological tissue for electroporation treatment, and a pulse generator electrically connected to the probe and configured to drive the electroporation probe using a sequence of one or more electric pulses to cause current transmission through the probe and induce a non-uniform electric field in the biological tissue proximate to the probe electrodes.

US2006/0009731 describes a transdermal delivery patch which includes an upper electrode, a lower electrode, and a drug storage area between two electrodes. An electric field between the two electrodes pushes a polar pharmaceutical compound in the drug storage area toward the skin and the lower electrode generates an ion channel for electroporation on the surface of the skin.

The effects and characteristics of the skin under a voltage bias has been extensively studied over the last 20 years. It is known that initial skin resistance starts between 50 k$\Omega$ and 100 k$\Omega$ but as the voltage across the top of the skin increases the resistance of the skin drops three orders of magnitude down to about 100$\Omega$. As long as skin resistance stays above 500$\Omega$, the pores that are created during the voltage pulse recover in a matter of seconds to minutes. By increasing the voltage and reducing the resistance below 500$\Omega$, the pores are considered to remain open and the cells are irreversibly damaged. A problem with conventional electroporation devices is that at voltages needed to effectively open the skin pores and allow transdermal delivery of actives damage to the skin can order.

US2002/0198512 discloses a method of electroporation of cells in target tissue performed using an injection apparatus comprising a shaft in the form of a needle having a substance delivery lumen therein. An electrode structure is disposed on the shaft near a delivery opening in the shaft which communicates with the lumen. A second electrode structure is located close to the first electrode structure either on the shaft or on a base and is separated from the first electrode by a small distance. Using a combination of injection of active agents via microneedles and electric fields, allows transdermal delivery to be achieved using relatively low voltages. A disadvantage of delivering an active agent through a hollow microneedle it is difficult to rapidly administer a clinically significant amount of drug through such needles. The capacity of microneedles to deliver active agents is limited due to the small size of the delivery orifices in the end of a microneedle and the low cross sectional area of the delivery lumen within the. Even with a high pressure within the needle and a high pressure gradient at the tissue-needle interface active agents can be delivered to tissues through the shaft of a microneedle at a low rate.

The present invention seeks to mitigate the above-mentioned problems. In particular the present invention seeks to provide for the rapid and stable delivery of active agents through the skin. Alternatively or additionally, the present invention seeks to provide for an improved method of electroporation in which a low a voltage can be applied between the two electrodes such that it treatment does not cause irreversible damage to the skin. The present invention also seeks to provide a method of transdermal delivery of an active agent having an efficacy that is independent of abnormalities on the skin surface such as skin surface contaminants from the environment, skin pH levels, hair thickness and density, sweat quality and quantity.

SUMMARY OF THE INVENTION

The present invention provides, according to a first aspect, an electrode assembly for transdermal delivery of an active agent, comprising:
  a penetrative electrode of one polarity configured to provide an electrical contact beneath the stratum corneum;
  a surface electrode of the opposite polarity configured to provide an electrical contact to the external surface of the skin;
  a dispenser configured to dispense the active agent to the external surface of the skin.

The penetrative electrode optionally comprises a plurality of microneedles. The term "microneedles" as used herein refers to needles that are from about 10 to about 200 µm in length. The electrode assembly may comprise a skin contact surface comprising the surface electrode. The dispenser may comprise an outlet configured to dispense the active agent to the external surface of the skin. The microneedles may project from the skin contact surface and are configured to be inserted into the skin of the human body. At least one of, a plurality of, and each of, the microneedles may comprises a shaft extending from a base on the skin contact surface to a tip. The exterior of the shaft may be electrically insulated and the tip may provide an electrical contact. The penetrative electrode and surface electrode are preferably electrically insulated from each other. Such an electrode assembly is advantageously configured so that, on placing the skin contact surface into contact with the skin of a human or animal body, the microneedles are inserted into the skin, such that the tips of the microneedles penetrate at least beyond the stratum corneum of the skin and both the surface electrode and any active agent dispensed from the outlet of the dispenser are in contact with the external surface of the skin.

For the avoidance of doubt, if the penetrative electrode comprises a plurality of microneedles, the dispenser is typically configured to dispense the active agent to the external surface of the skin without the active agent passing through the microneedles.

The invention further provides for the use of an electrode assembly of the first aspect of the invention for transdermal delivery of an active agent to the tissue of a human or animal body.

In a second aspect of the invention, the invention provides a method of transdermal delivery of an active agent to the tissue of a human or animal body.

The method of the second aspect of the invention may, for example, be a method for the transdermal delivery of an active agent to human or animal tissue, for example by electroporation, the method comprising:
  providing an electrical contact of a penetrative electrode beneath the stratum corneum of the skin of the human or animal body;
  providing an electrical contact of a surface electrode on the external surface of the skin of the human or animal body;
  providing an active agent in contact with the skin; and
  applying a voltage differential between the penetrative electrode and the surface electrode across the stratum corneum.

Application of a voltage differential between the electrical contact of the penetrative electrode and surface electrode has been found to facilitate transport of the active ingredient from the skin surface across the stratum corneum. The active ingredient is advantageously transported from the skin surface across the stratum corneum on application of the voltage differential between the electrical contact of the penetrative electrode and surface electrode.

The method of the second aspect of the present invention may use the electrode arrangement of the first aspect of the present invention or the transdermal delivery system of the third aspect of the present invention which is described below. For the avoidance of doubt, if the penetrative electrode comprises a plurality of microneedles, the active agent is transported through the stratum corneum of the skin without the active agent passing through the microneedles.

In a third aspect, the invention provides a transdermal delivery system comprising the electrode assembly according to the first aspect of the invention wherein an active agent is present in the dispenser.

In the electrode arrangement of the first aspect of the present invention and the transdermal delivery system of the third aspect of the present invention, the dispenser may, for example, be in the form of a patch. The patch may be arranged to be present on a skin contact surface adjacent to the surface electrode during use. The dispenser preferably comprises an outlet arranged to contact the surface of the skin in use and optionally deliver the active agent to the external surface of the skin.

The transdermal delivery system of the third aspect of the invention is preferably suitable for use in the method of the second aspect of the invention.

In the electrode assembly of the first aspect of the invention, the method of the second aspect of the invention, and the delivery system of the third aspect of the invention, the penetrative electrode optionally comprises microneedles configured to be inserted into the skin of the human or animal body, the microneedles each comprising a base, a shaft and a tip, wherein the shafts extend from the bases to the tips, wherein the exterior of the shafts is electrically insulated, and wherein the tips provide the electrical contact. The method of the second aspect of the invention advantageously comprises providing an active ingredient in the dispenser of an electrode assembly of the first aspect of the invention that optionally comprises microneedles extending from a skin contact surface, placing the skin contact surface of the electrode assembly in contact with the skin of a human or animal body such that the microneedles are inserted into the skin and such that the surface electrode and the active agent contacts the surface of the skin, and applying a potential difference between the tips of the microneedles of the penetrative electrode and the surface electrode. The method of the second aspect of the invention advantageously comprises the steps of inserting the penetrative electrode of the transdermal delivery system of the third aspect of the invention into the skin of the human or animal body, positioning electrical contacts of the surface electrode on the external surface of the skin on the opposite side of the stratum corneum to the penetrative electrode, positioning the an outlet of the dispenser for delivery of an active agent to the external surface of the skin adjacent to the surface electrode and applying a potential difference across the stratum corneum (e.g. through the thickness of the stratum corneum) between the penetrative electrode and the surface electrode. The method may comprise the step of dispensing the active agent to the surface of the skin, e.g. through an outlet of a dispenser. In the electrode assembly of the first aspect of the invention and the delivery system of the third aspect of the invention, a suction head is advantageously provided configured to provide suction to the external surface of the skin. The electrode assembly optionally comprises a suction zone. The suction head is advantageously configured to apply suction to a suction zone within which suction zone the penetrative electrode and surface electrode are optionally provided, and optionally mounted. The method of the second aspect of the invention advantageously includes the step of applying suction to the external surface of the skin, e.g. from a suction head. Advantageously, the suction head is arranged to provide suction to a suction zone that surrounds the penetrative electrode and the surface electrode. Suction is advantageously applied to the surface of the skin adjacent to the penetrative electrode, e.g. from a suction head. The suction head is advantageously arranged to apply suction to the skin around the location where penetrative electrodes penetrate the external surface of the skin. The electrode assembly is advantageously configured to apply a partial vacuum to a region of the external surface of the skin of a human or animal in use. The partial vacuum is advantageously applied to the skin within an area defined by the suction zone. The suction zone may, for example, be bounded by a perimeter. In use, the perimeter of the suction zone advantageously contacts the skin and forms a seal. A partial vacuum may, for example, be formed in the area bounded by a perimeter by applying suction through the suction head. The penetrative electrode and surface contact electrode are advantageously provided within the suction zone, i.e. within the perimeter of the suction zone. The perimeter of the suction zone may constitute a part of a skin contact surface of the electrode assembly or delivery device of the invention. A sealing member may be provided to form a seal between the skin and the suction head, optionally thereby forming said perimeter. The sealing member may be deformable, for example elastically deformable, so as to facilitate formation of a seal between the suction zone and the skin. At least a part of the skin contact surface is within the suction zone. The entirety of the skin contact surface may be within the perimeter of the suction zone. In use, at least a part of the skin contact surface of the electrode assembly or delivery device of the invention that is within the suction zone contacts the external surface of the skin. Advantageously, a reduced pressure (e.g. a partial vacuum) is applied between the skin contact surface that is within the suction zone and the external surface of the skin adjacent to the suction zone. The suction head may include one or more (for example, three) suction nozzles. The suction nozzle advantageously extracts air from the suction head thereby lowering the pressure within the suction zone. The provision of suction to the skin has been found to aid penetration of the penetrative electrode. The provision of suction may attach the suction head to the skin. The provision of suction to the skin has been found to facilitate the maintenance of continued contact between the electrode assembly or delivery system and the skin, thereby enabling a stable continuous delivery of active agent and/or continuous electrical contact between the surface electrode and the external surface of the skin.

When the penetrative electrode includes a plurality of microneedles, application of suction to the external surface of the skin, e.g. to a suction zone, has been found to facilitate the insertion of the microneedles into the external surface of the skin. The bases of the microneedles advantageously extend from a part of the skin contact surface that is within the suction zone. When suction is applied to the skin, the surface of the skin, e.g. the part of the surface of the skin bounded by the perimeter of the suction zone, may be distorted. Advantageously, the microneedles are angled to penetrate the skin in a perpendicular manner as the skin is distorted. The application of suction to distort the surface of the skin advantageously stretches the skin thereby thinning the stratum corneum. As a result the distance the active agent must travel to transverse the stratus cornea is reduced, thereby facilitating higher transdermal throughput. Also as a result the depth to which that the penetrative electrode must penetrate the skin to provide an electrical contact beneath the stratum corneum is reduced.

The penetrative and surface electrodes of the electrode assembly of the first aspect of the invention and the delivery system of the third aspect of the invention are advantageously electrically isolated from one another. It is also found that the provision of insulated electrodes above and below the stratum corneum provides for electroporation using an electric field of reduced strength which has safety advantages. Without wishing to be bound by theory, the present inventors believe that by positioning selectively insulated electrodes either side of the stratum corneum, an electric double layer capacitor is created which enables a controlled pulsed electric field to be applied across the stratum corneum opening skin cells and allowing active agents, such as bioactive materials, to permeate into the lower skin layers, such as the epidermis, dermis, and subcutaneous lipid layers.

The inventors have found that the application of an electrical potential between an electrical contact of a penetrative electrode positioned beneath the stratum corneum and a surface electrode positioned on the external surface of the surface electrode, wherein the electrical contact of a penetrative electrode and the surface electrode are electrically insulated from each other, is effective in proving electroporation at a low electrical potential. The positioning of the electrical contacts on either side of the stratum corneum has been found to provide for the reversible opening of pores creating a transcorneocyte transport route through the cell and lipids using a relatively low voltage, e.g. of 100 V or less. The positing of the electrical contacts advantageously optimises the effectiveness of the electrical charge across the stratum corneum thus providing reversible pore opening without lasting damage to the skin. The application of a low potential difference over a prolonged period using the assembly and method of the invention has been found to not be detrimental to the human or animal body allowing for sustained continuous delivery of active agents to the body. The electrode assembly of the first aspect of the invention, the method of the second aspect and the delivery system of the third aspect of the invention, have also been found to allow significant volumes of active ingredient to be delivered to the human or animal body through contact of the active agent present in the dispenser with the exterior surface of the skin across a large contact area. In particular the electrode assembly, delivery system and method of the invention have been found to enable higher volumes per unit area of active agents to be delivered through the stratum corneum than can be achieved by a device that relies on injection of the active agents through hollow microneedles.

In an electrode assembly of the first aspect of the invention which comprises microneedles, the electrical contacts provided by the microneedle tips and the surface electrode are advantageously configured to be positioned on either side of the stratum corneum, allowing a voltage differential applied between the two electrodes to be concentrated across the stratum corneum. Similarly, in the transdermal delivery system of the third aspect of the invention, the electrical contact of the penetrative electrode beneath the stratum corneum and the electrical contact of the surface electrode allows a voltage differential applied between the two electrodes to be concentrated across the stratum corneum. Advantageously, application of the voltage differential between the penetrative electrode and surface electrode facilitates formation of an electrical double layer capacitor. Without wishing to be bound by theory, the inventors believe that the provision of a pair of electrodes that are electrically isolated from each other having opposite polarities and being positioned on either side of the stratum corneum advantageously enables the creation of a double layer capacitor across the skin, or more specifically across the stratum corneum, as a voltage is applied.

The electrode assembly of the first aspect of the invention, the method of the second aspect of the invention and the delivery system of the third aspect of the invention, advantageously provides an electrical field orientated across the stratum corneum, preferably substantially perpendicular to the stratum corneum, on application of a potential difference between the penetrative electrode and surface electrode. The inventors have found that the application of an electrical potential between an electrical contact of a penetrative electrode positioned below and beyond the stratum corneum and a surface electrode positioned on the external surface of the skin, wherein the electrical contact(s) of the penetrative electrode and the surface electrode are electrically insulated from each other, in the assembly of the first aspect of the invention, the method of the second aspect of the invention and the delivery system of the third aspect of the invention, is effective in providing an electrical field orientated substantially perpendicular to the stratum corneum. The voltage difference that is applied across the stratum corneum advantageously creates a charge gradient across the stratum corneum. The stratum corneum has a high electrical resistance and therefore generating an electric field orientated parallel to the stratum corneum, as in some known devices, is disadvantageous because higher voltages are then required to open up path ways. It is believed that by generating an electric field substantially perpendicular to the stratum corneum, as in the present invention, the voltage difference needed to open up path ways effect transport of the active agent across the stratum corneum is reduced.

Advantageously, when the electrode assembly of the first aspect of the invention comprises a plurality of microneedles, the shafts of the microneedles are configured to be in a direction perpendicular (normal) to the skin contact surface in use. Advantageously, the electrode assembly is configured to provide an electrical field orientated coaxial to the shafts of the microneedles on application of a potential difference between the penetrative electrode and surface electrode. The electrical isolation of the two electrodes from each other and the insulation of the shaft of the microneedles from the tissue they penetrate has been found to be important in creating an electrical field orientated perpendicular to the stratum corneum. The microneedles are advantageously arranged to penetrate the skin in a direction substantially perpendicular to the stratum corneum. As such, the microneedles traverse the depth of stratum cornea across the shortest distance. When the electrode assembly or delivery device of the invention comprises a suction head that distorts the surface of the skin on application of suction, the microneedles may be oriented to accommodate the distortion of the skin. For example, the microneedles may be oriented to penetrate the distorted skin in a direction substantially perpendicular to the stratum corneum when the skin is distorted. For example, the microneedles may be tilted with respect to one another such that each microneedle is configured to penetrate the distorted skin in a direction perpendicular to the stratum corneum.

The resistance of the stratum corneum varies from person to person, e.g. from about $5 \times 10^4$ ρ to about $1.5 \times 10^5$ ρ (50 kΩ·m to 150 kΩ·m) depending on factors including skin type, hydration, cleanliness, sweat production, etc. Without wishing to be bound by theory, the inventors believe that the electrode assembly of the first aspect of the invention, the method of the second aspect of the invention and the delivery system of the third aspect of the invention, in which the electrodes focus the electric field perpendicular to the stratum corneum (i.e. apply a charge straight down through the surface of the skin) has been found to eliminate stray capacitances and leakage currents on the surface between the electrodes. As such a lower voltage than has been used in previous electroporation assemblies has been found to be effective in opening the skin pores. The method and delivery system of the invention has also been found to be operable with a lower contact pressure between the active agent and the skin than in known electroporation devices and methods.

If a plurality of microneedles is provided, the shafts of the microneedles of an electrode assembly according to the first aspect of the invention may conduct electricity to the tips. An electrically conducting material may be present in the interior of the shafts to conduct electricity to the tips. The shafts of the microneedles advantageously comprise electrically insulated surfaces and electrically conductive cores that communicate with the tips. The cores comprise an electrically conductive material. The electrically conductive material preferably has a conductivity of at least $3.0 \times 10^7$ σ (S/m) at 20° C., preferably at least $4.0 \times 10^7$ σ at 20° C., especially at least $5.0 \times 10^7$ σ at 20° C. The electrically conductive material may have a conductivity in the range of $3.0 \times 10^7$ to $1.0 \times 10^{10}$ σ (S/m) at 20° C. The electrically conducting material is advantageously biocompatible with the human and/or animal body. The conducting material may, for example, comprise stainless steel, titanium, gold, or alloys thereof or diamond-like carbon (DLC). All exterior surfaces of the penetrative electrode other than the electrical contact are advantageously electrically insulated. Advantageously, the only part of the entire electrode assembly that, in use, has the polarity of the penetrative electrode and is in contact with the skin, is the electrical contact of the penetrative electrode.

The electrode assembly of the first aspect of the invention and the delivery system of the third aspect of the invention include a surface electrode. The surface electrode is configured to contact the external surface of the skin in use, for example, in use in accordance with the method of the second aspect of the invention. The surface electrode may comprise a plurality of electrical contacts each configured to contact, and transmit electrical charge to, the external surface of the skin in use.

The electrode assembly of the first aspect of the invention and the delivery system of the third aspect of the invention may include a skin contact surface which comprises the electrical contact(s) of the surface electrode and the dispenser outlet configured to dispense the active agents to the skin. The dispenser may, for example, be in the form of a patch configured to deliver an active agent to the external surface of the skin. The entire skin-contacting surface of the electrode assembly of the first aspect of the invention and the delivery system of the third aspect of the invention, other than the electrical contact of the penetrative electrode and the electrical contact of the surface electrode may be electrically insulated. The entire skin-contacting surface of an electrode assembly of the first aspect of the invention that comprises a plurality of microneedles, other than the tips of the microneedles and the surface electrode, may be electrically insulated. The surface of the shafts of the microneedles present in an electrode assembly of the first aspect of the invention is advantageously non-conductive. The entire surface of the shafts of the microneedles between the bases and the tips may, for example, be electrically insulated. The skin-contacting surface of the electrode assembly and the delivery system other than the electrical contacts is optionally of an electrically non-conductive, insulating material. For example, the surfaces of the shafts of microneedles present in an electrode assembly are optionally of an electrically non-conductive, insulating material. The insulating material may have a resistivity of at least $1.0 \times 10^8 \rho$ ($\Omega \cdot m$) at 20° C., preferably at least $1.0 \times 10^{10} \rho$ at 20° C., especially at least $1.0 \times 10^{12} \rho$. The material may, for example, comprise ZnO or SiN or parylene.

When the electrode assembly of the first aspect of the invention comprises a plurality of microneedles, the shafts of the microneedles advantageously have a maximum width (or diameter in the case of a circular cross section) of from 0.02 to 50 µm or 0.05 to 35 µm, especially of from 0.02 to 20 µm, such as from 0.04 to 10 µm, preferably from 0.05 to 8 µm. Narrow widths, e.g. of less than 25 µm, especially 10 µm or less, are particularly preferred in order to minimise discomfort when the penetrative electrode is inserted into the skin. In the electrode assembly of the first aspect of the invention the active agent is delivered to the body from the dispenser to the external surface of the skin rather than via the microneedles. Unlike prior art devices, microneedles of the electrode assembly of the present invention do not typically incorporate a conduit for conveying the active agent along the shafts. Thus, the shafts of the microneedles may be narrow, e.g. having a width of 25 µm or less. In the transdermal delivery system of the third aspect of the invention, the active agent is delivered from the dispenser through the external surface of the skin and not via mechanical insertion through the stratum corneum. The delivery of the active ingredient to the skin may be accomplished across a large contact area in the delivery system of the present invention, thereby allowing for higher transport rates that can be achieved through delivery through the shafts of microneedles. Thin micro needles in the electrode assembly and delivery system of the invention allow a higher density of needles per cm² to penetrating the skin surface. Thicker micro needles, e.g. those designed to deliver active agents through the shaft, will not penetrate the surface if the needle array is too densely populated.

In the assembly of the first aspect of the invention, the method of the second aspect of the invention and the delivery system of the third aspect of the invention, the electrical contact of the penetrative electrode is optionally at least 10 µm from a skin contact surface (i.e. a surface configured to rest on the external surface of the skin in use), preferably at least 30 µm. As nerve endings can be as close as 50 µm to the surface of the skin, the penetrative electrode preferably penetrates into the skin by no more than 50 µm. The maximum distance the electrical contact(s) of the penetrative electrode projects from a skin contact surface is optionally no more than 500 µm, such as no more than 350 µm. Typically the maximum distance the electrical contact(s) of the penetrative electrode projects from a skin contact surface is no more than 200 µm, such as no more than 150 µm, especially no more than 100 µm, preferably no more than 80 µm, more preferably no more than 50 µm. The electrical contact of the penetrative electrode may, for example, be from 10 to 500 µm such as from 10 to 350 µm. Typically the electrical contact of the penetrative electrode is from 10 to 200 µm, such as from 20 to 150 µm, especially from 25 to 100 µm, preferably from 30 to 80 µm from a skin contact surface. The electrical contact(s) of the penetrative electrode are optionally at least 15 µm, preferably at least 35 µm, from the nearest electrical contact(s) of a surface electrode. The maximum distance from an electrical contact of the penetrative electrode to the nearest electrical contact of a surface electrode is optionally no more than 200 µm, such as no more than 150 µm, especially no more than 100 µm, preferably no more than 85 µm. The distance between the electrical contact of the penetrative electrode and the nearest electrical contact of a surface electrode may, for example, be from 10 to 200 µm in length, such as from 20 to 150 µm in length, especially from 25 to 100 µm in length, preferably from 30 to 80 µm in length. In an assembly of the first aspect of the invention that comprises microneedles, the microneedles are optionally at least 10 µm in length, preferably at least 30 µm in length from the base to the tip. As nerve endings can be as close as 50 µm to the surface of the skin, the penetrative electrode microneedles preferably penetrate into the skin nor more than 50 µm. The maximum length of penetrative electrode microneedles is optionally no more than 500 µm or 350 µm, typically no more than 200 µm, such as no more than 150 µm, especially no more than 100 µm, preferably no more than 80 µm, more preferably no more than 50 µm. The microneedles may, for example, be from 10 to 500 µm in length or 10 to 200 µm in length, such as from 20 to 150 µm in length, especially from 25 to 100 µm in length, preferably from 30 to 80 µm in length. The microneedles may, for example, be from 10 to 200 µm in length, such as from 20 to 150 µm in length, especially from 25 to 100 µm in length, preferably from 30 to 80 µm in length.

Advantageously, the electrical contacts of the surface electrode and the outlet(s) of the dispenser for the active agent are dispersed across the skin contact surface. The electrode assembly may comprise a plurality of microneedles, for example 5 or more microneedles, such as 10 or more microneedles, especially 20 or more microneedles. Advantageously, the penetrative electrode comprises a plurality of microneedles the bases of which are interspersed amongst electrical contacts of the surface electrode and the outlet(s) of the dispenser across the skin contact surface. Advantageously, at least a portion of the outlet(s) of the dispenser for the active agent is situated between the base of the shaft of a microneedle and an electrical contact of the surface electrode. The outlet of the dispenser may, for example, substantially surround the base of at least one microneedle. The outlet(s) of the dispenser for the active agent are optionally interspersed between the bases of the microneedles. The microneedles may be dispersed across a skin contact surface of the electrode assembly. The microneedles may be present on the skin contact surface at a density of at least 5 microneedles per cm², such as 10 microneedles per $cm^2$, for example 20 per $cm^2$, especially 50 per $cm^2$. The plurality of microneedles may, optionally, be arranged in rows. The surface electrode may, optionally, be arranged between the bases of the rows of microneedles. The outlet(s) of the dispenser for the active agent may, optionally, be arranged between the bases of the rows of microneedles.

The electrode assembly, delivery system and method of the invention have been found to be effective in opening the skin pores allowing delivery of the active agent through the skin as a voltage is applied. The provision of a penetrative electrode of one polarity that provides an electrical contact beneath the stratum corneum and a surface electrode of the opposite polarity that provides an electrical contact to the external surface of the skin on the opposite side of the stratum corneum to the penetrative electrode, for example through the provision of multiple microneedles each bearing a tip that provides the electrical contact of one polarity and a surface electrode having electrical contacts of the opposite polarity that are distributed across a skin contact surface, advantageously provides an electrical field orientated perpendicular to the stratum corneum that is evenly distributed across a large area. Accordingly, an active agent applied to the skin across a large area may advantageously be delivered across the skin using the electrode assembly, delivery system and method of the invention.

The active agent delivered by the electrode assembly, delivery system and method of the invention may comprise a charged molecule, e.g. an ionic or zwitterionic molecule. The active agent is advantageously applied to the skin from a dispenser outlet (e.g. a patch) present around the base of the penetrative electrode, such as around the bases of a plurality of microneedles that constitute a part of the penetrative electrode. It has been found to be important that the electrical contacts of the penetrative electrode and the surface electrode are electrically isolated from one another. For example, the shafts of the microneedles are electrically insulated to prevent charge being conducted from the electrical contact of the penetrative electrode to the surface electrode via the electrode assembly thus creating a short circuit.

The electrode assembly and delivery system of the invention advantageously comprise an electric double layer capacitor configured to apply a voltage differential between the tips of the microneedles of the penetrative electrode and the surface electrode across the stratum corneum. Optionally, the electric double layer capacitor is configured to vary the voltage differential between the tips of the microneedles of the penetrative electrode and the surface electrode across the stratum corneum.

Advantageously, the electrical contact(s) of the penetrative electrode of the electrode assembly or delivery system of the invention has an uneven or irregular surface. The electrical contact of the penetrative electrode may, for example, have a permeable surface. The electrical contact of the penetrative electrode may, for example, have a porous surface. When the penetrative electrode comprises microneedles, the tips of microneedles advantageously have an uneven or irregular surface. The tips of microneedles advantageously have a permeable surface, for example a porous surface. The provision of an uneven or irregular surface to the electrical contact(s) of the penetrative electrode increases the surface area has been found to provide for an enhanced electrical contact.

The electrode assembly of the first aspect of the invention and the delivery system of the third aspect of the invention have been found to be particularly useful in continuous transdermal delivery of the active agent. In the method of the second aspect of the invention, the active agent is advantageously continuously transdermally delivered to a tissue of the human or animal. For example, the active agent may be continuously delivered across the skin for 10 minutes or longer, such as for 30 minutes or longer, especially for 1 hour or longer. In some embodiments the electrode assembly may be used to continuously deliver an active agent across the skin for 2 hours or longer, such as for 4 hours or longer.

The electrode assembly includes a dispenser configured to dispense an active agent to the skin surface. When an active agent is present in the dispenser of the electrode assembly of the first active agent, a patch configured to deliver an active agent to the external surface of the skin may be formed. The dispenser preferably includes an outlet which is present at a skin contact surface of the electrode assembly or transdermal delivery system and from which outlet the active agent may be delivered to the external surface of the skin. For the avoidance of doubt, the electrode assembly advantageously only includes dispensers configured to deliver the active agent to the external surface of the skin and does not include additional dispensers configured to deliver the active agent from outlets positioned beneath the external surface of the skin.

In the method of the second aspect of the present invention, the step of providing an electrical contact of a penetrative electrode beneath the stratum corneum of the skin of the human or animal body in the method of the second aspect of the invention advantageously comprises inserting the penetrative electrode into the skin of the human body such that the electrical contact extends at least beyond the stratum corneum. When the penetrative electrode includes microneedles, the step of providing an electrical contact of a penetrative electrode at least beyond the stratum corneum of the skin of the human or animal body in the method of the second aspect of the invention may advantageously comprise inserting the microneedles into the skin of the human or animal body such that the tips of the microneedles that provide an electrical contact extend at least beyond the stratum corneum.

The electrode assembly of the first aspect of the invention and the delivery system of the third aspect of the invention may comprise an electrical circuit configured to apply a voltage differential between the electrical contact of the penetrative electrode and the electrical contact of the surface electrode. When the penetrative electrode comprises microneedles, the electrode assembly and the delivery system may comprise an electrical circuit configured to apply a voltage differential between the tips of the microneedles of the penetrative electrode and the surface electrode. The electrical circuit may be or may comprise a double layer capacitor. In the method of the second aspect of the invention, a voltage differential is applied between the electrical contact of the penetrative electrode and the electrical contact surface electrode. The potential difference applied between the electrical contact of the penetrative electrode and the surface electrode is advantageously less than 100 V, for example less than 90 V, such as less than 80 V, especially less than 70 V. In some embodiments the potential difference applied between the penetrative electrode and the surface electrode is less than 65 V such as less than 60 V, especially less than 50 V. In some embodiments, the potential difference (e.g. the maximum potential difference) applied between the penetrative electrode and the surface electrode is at least 5 V such as at least 10 V, especially at least 20 V or at least 30 V. The voltage differential between the electrical contact of the penetrative electrode and the surface electrode across the stratum corneum may be varied in the method of the second aspect of the invention. The electrode assembly of the first aspect of the invention and delivery system of the third aspect of the invention, advantageously comprises means to vary the voltage applied between the penetrative electrode (for example, the electrically conductive tips of the microneedles of the electrode assembly) and the surface electrode.

It will of course be appreciated that features described in relation to one aspect of the present invention may be incorporated into other aspects of the present invention. For example, the method of the second aspect invention may incorporate any of the features described with reference to the electrode assembly of the first aspect of the invention or delivery system of the third aspect of the invention and vice versa. Similarly, the transdermal delivery system of the third aspect of the invention may incorporate any of the features described with reference to the electrode assembly of the first aspect of the invention and vice versa.

DESCRIPTION OF THE DRAWINGS

Embodiments of the present invention will now be described by way of example only with reference to the accompanying schematic drawings of which.

DETAILED DESCRIPTION

Whilst the present invention has been described and illustrated with reference to particular embodiments, it will be appreciated by those of ordinary skill in the art that the invention lends itself to many different variations not specifically illustrated herein. By way of example only, certain possible variations will now be described.

Figure 1:
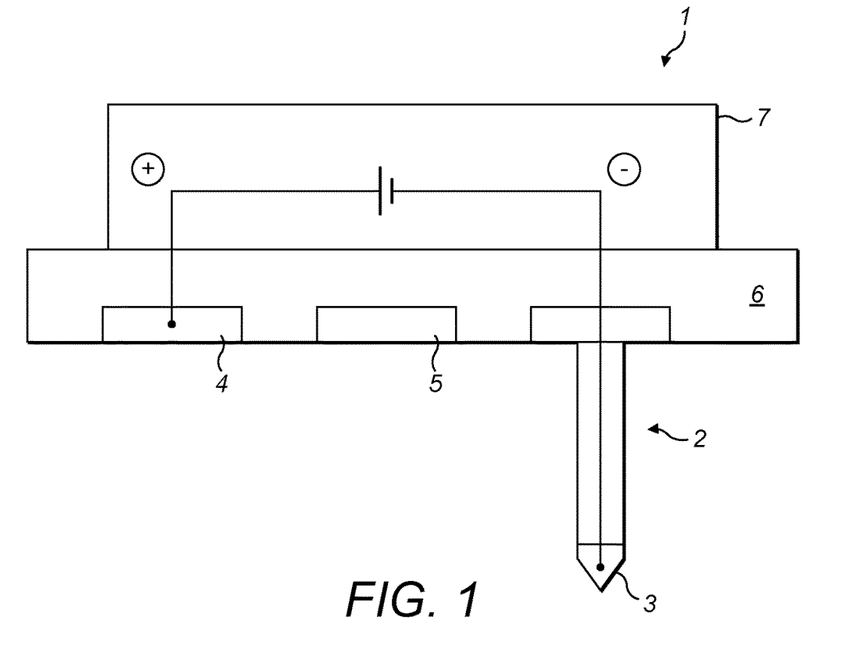
FIG. 1 shows a transdermal delivery system according to a first embodiment of the invention.

In a first embodiment shown in FIG. 1, the invention provides a transdermal delivery system (1) for delivering an active agent to human or animal tissue, comprising: a penetrative electrode (2) of one polarity configured to provide an electrical contact (3) beneath the stratum corneum; a surface electrode (4) of the opposite polarity to that of the penetrative electrode (2) that provides an electrical contact to the external surface of the skin on the opposite side of the stratum corneum to the electrical contact (3) of the penetrative electrode (2); and a dispenser in the form of a patch (5) configured to deliver of an active agent to the external surface of the skin adjacent to the surface electrode (4). The delivery device also comprises a mounting (6) configured to mount the surface electrode (4) and the patch (5) in a position whereby they contact the external surface of the skin in use. The penetrative electrode (2) extends from the mounting (6) such that in use, the penetrative electrode (2) is inserted into the skin of a human or animal body such that the electrical contact (3) of the penetrative electrode (2) is positioned beneath the stratum corneum of the human or animal. A housing (7) includes electrical circuitry configured to provide a potential difference between the surface electrode (4) and the electrical contact (3) of the penetrative electrode (2), thereby generating an electrical field. In the embodiment of FIG. 1, the surface electrode (4) is positively charged and the electrical contact (3) of the penetrative electrode (2) is negatively charged.

Figure 2:
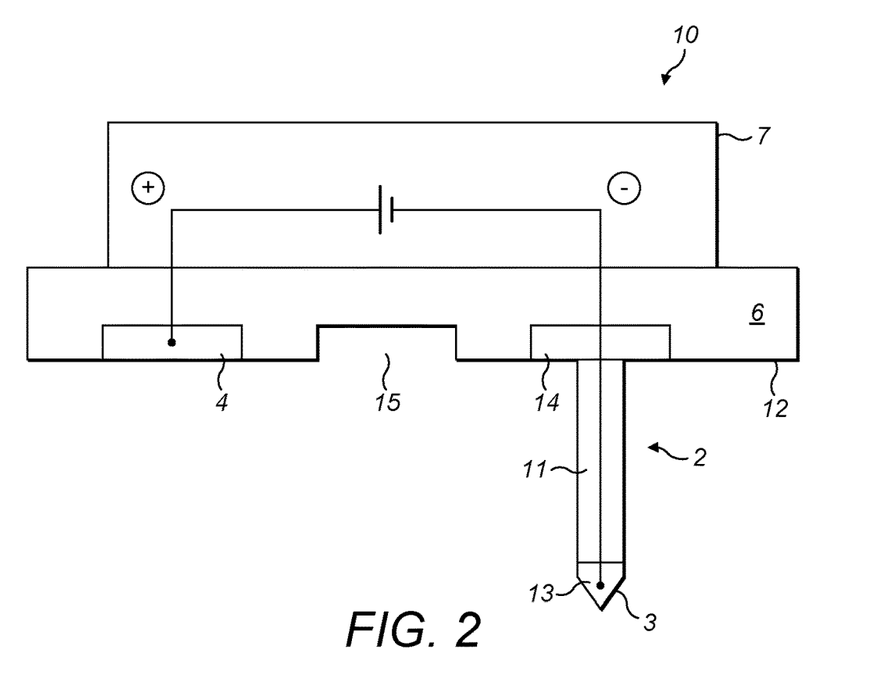
FIG. 2 shows an electrode assembly according to a second embodiment of the invention.

In a second embodiment shown in FIG. 2, the present invention provides an electrode assembly (10) for transdermal delivery of an active agent. The electrode assembly (10), comprises a penetrative electrode (2) of one polarity comprising microneedles having a shaft (11), a tip (13) and a base (14). The electrode assembly (10) also comprises a skin contact surface (12) comprising a surface electrode (4) of the opposite polarity to the penetrative electrode (2) and a dispenser outlet (15) configured to dispense an active agent to the external surface of the skin. The microneedles project from the skin contact surface (12) and are configured to be inserted into the skin of the human body. The shaft (11) of the microneedles extends from a base (14) on the skin contact surface (11) to a tip (13). The exterior of the shaft (11) is electrically insulated and the tip (13) provides an electrical contact (3). The penetrative electrode (2) and surface electrode (4) are electrically insulated from each other. The assembly (10) is configured such that, on placing the skin contact surface (12) into contact with the skin of a human or animal body, the microneedles are inserted into the skin, such that the tips (13) of the microneedles penetrate at least beyond the stratum corneum of the skin and both the surface electrode (4) and any active agent dispensed from the outlet (15) contacts the external surface of the skin. The electrode assembly (10) also comprises a mounting (6) configured to mount the surface electrode (4) and the outlet (15) in a position whereby they contact the external surface of the skin in use. The microneedles of the penetrative electrode (2) extend from the mounting (6) such that in use, the microneedles are inserted into the skin of a human or animal body so that the electrical contact (3) provided by the tip (13) is positioned beneath the stratum corneum. A housing (7) includes electrical circuitry to provide a potential difference between the surface electrode (4) and the electrical contacts (3) of the tips (13), thereby generating an electrical field.

Figure 3:
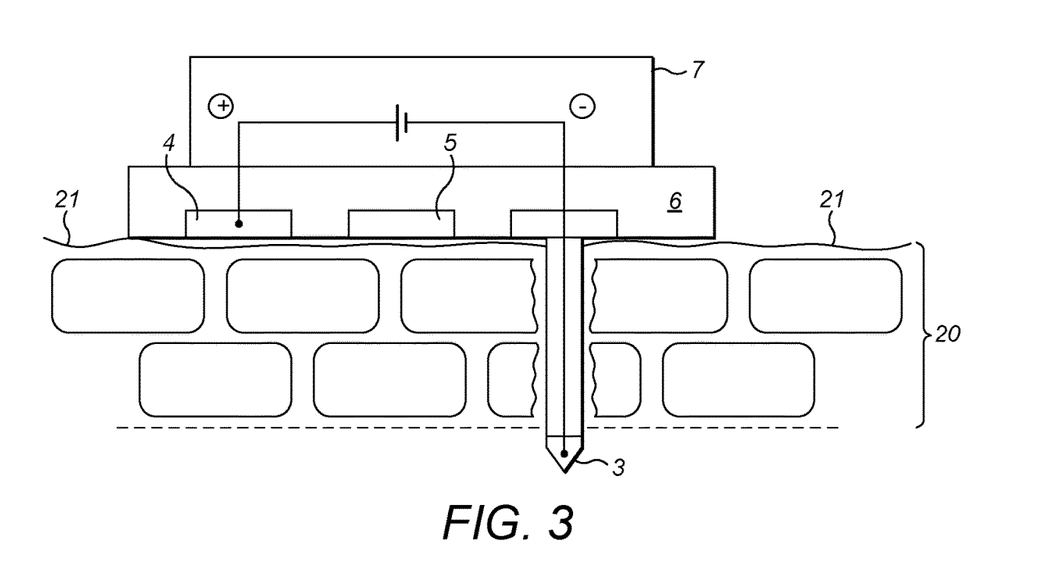
FIG. 3 shows the transdermal delivery system according to a first embodiment of the invention and the electrode assembly according to a first embodiment of the invention in use.

FIG. 3 shows a transdermal delivery system (1) of the first embodiment in use, which transdermal delivery system (1) includes an electrode assembly (10) of the second embodiment. The electrical contact (3) of the penetrative electrode (2) has been inserted into the skin of the human or animal body such that the electrical contact (3) is situated beneath the stratum corneum (20) of the skin; an electrical contact of a surface electrode (4) is on the external surface (21) of the skin; the active agent of the patch (5) is in contact with the skin; and a voltage differential is applied between the penetrative electrode (2) and the surface electrode (4). The voltage differential between the electrical contact (3) of the penetrative electrode (2) and surface electrode (4) facilitates transport of the active ingredient from the skin surface across the stratum corneum (20).

Figure 4:
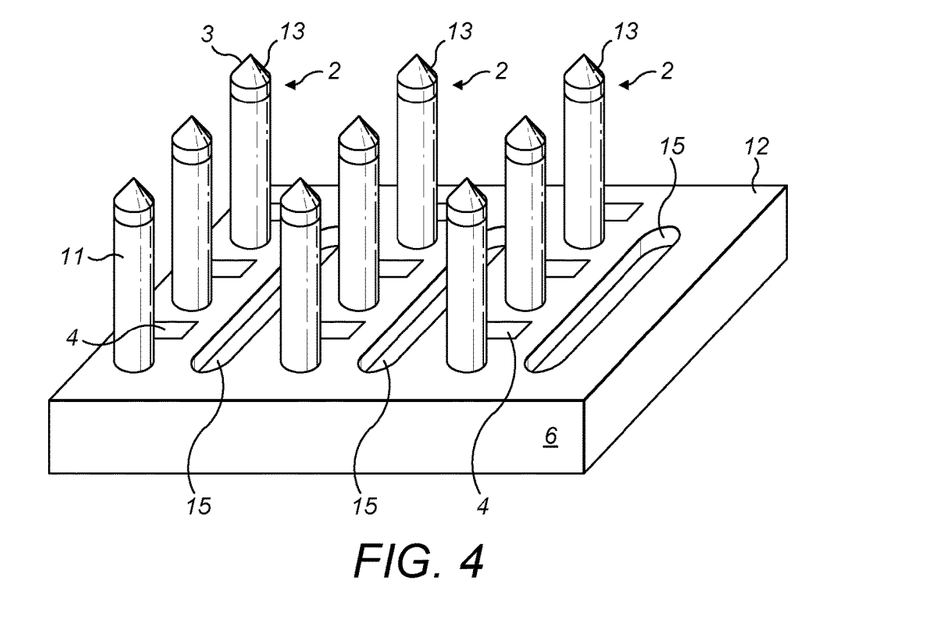
FIG. 4 shows an electrode assembly according to a third embodiment of the invention.

FIG. 4 shows a third embodiment electrode of an assembly of the invention in which the penetrative electrode (2) comprises an array of nine microneedles, each comprising a shaft (11) and a tip (13), the shafts (11) extending from a skin contact surface (12) of a mounting (6). A portion of the skin contact surface (12) is formed of by a surface electrode (4) having a plurality of electrical contacts, A further portion of the skin contact surface 12 is formed by outlets (15) of a dispenser configured to dispense an active agent. The microneedles of the penetrative electrode (2) are arranged in rows, with the electrical contacts of the surface electrode (4) dispersed between the rows of microneedles of the penetrative electrodes (2). The outlets (15) are also dispersed across the skin contact surface (12) between the rows of microneedles of the penetrative electrodes (2). In use, an electric field is generated between the electrical contacts (3) of the microneedles of the penetrative electrodes (2) and the electrical contacts of the surface electrode (4) which are of opposite polarity. The electric field is orientated substantially parallel to the shafts (11) of the microneedles of the penetrative electrode (2).

Figure 5:
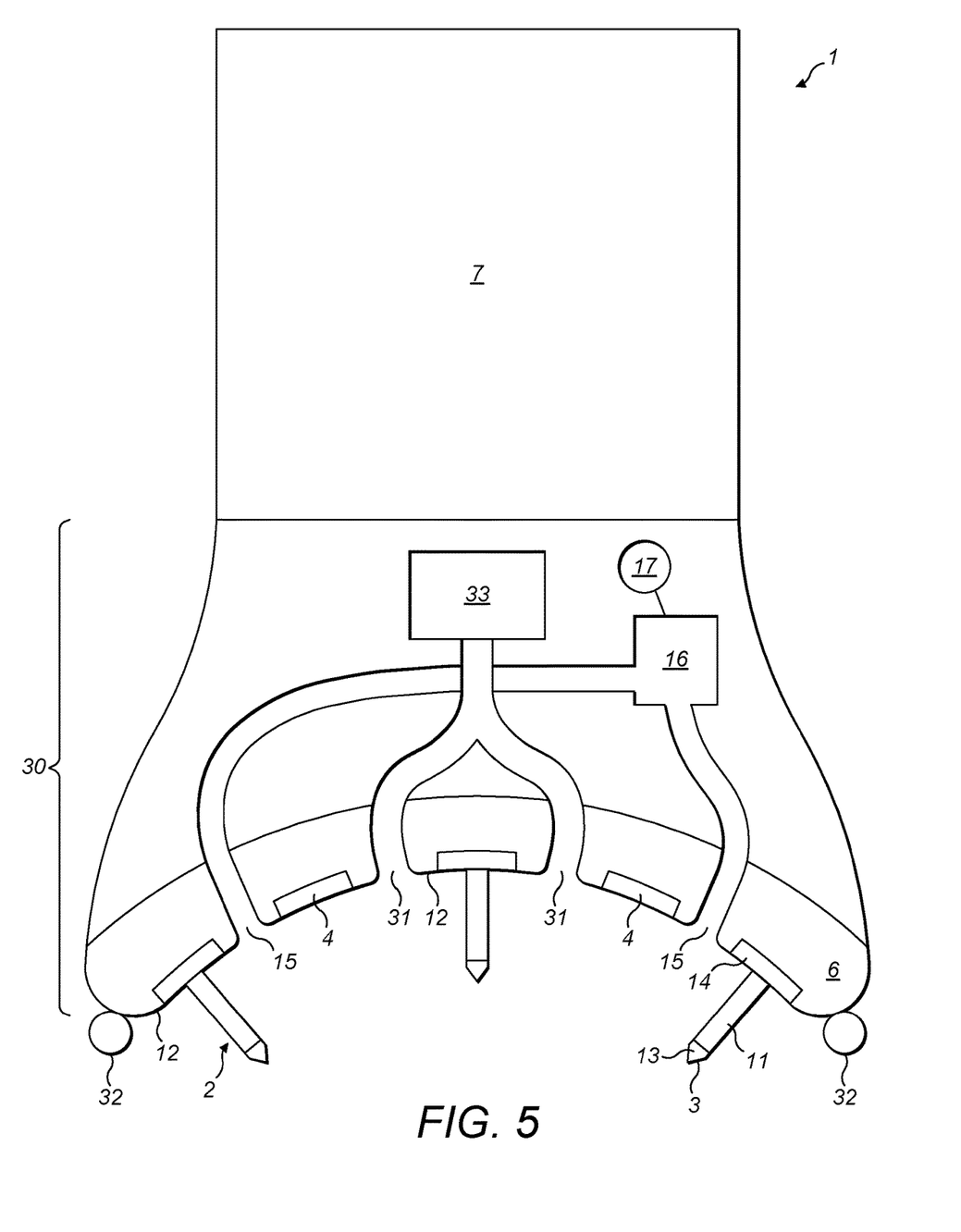
FIG. 5 shows a transdermal delivery system according to a fourth embodiment of the invention.

In a fourth embodiment shown in FIG. 5, the invention provides a transdermal delivery system (1) for delivering an active agent to human or animal tissue, comprising a suction head (30) having a skin contact surface (12) from which a plurality of penetrative electrode (2) having a plurality of microneedles extend. The microneedles of the penetrative electrode (2) include tips (13) having electrical contacts (3). The skin contact surface (12) also includes a surface electrode (4) having electrical contacts of the opposite polarity to that of the electrical contacts (3) of the penetrative electrodes (2). The electrical contacts of the surface electrode (4) provides conducts an electrical charge to the external surface of the skin on the opposite side of the stratum corneum to the electrical contacts (3) of the penetrative electrode (2) in use. The skin contact surface (12) further includes delivery outlets (15) configured to deliver an active agent to the external surface of the skin adjacent to the surface electrode (4), suction nozzles (31) configured to apply suction and generate a suction zone; and a sealing member (32) that forms a perimeter to the suction zone. The suction head (30) also comprises a mounting (6) configured to mount the electrical contacts of the surface electrode (4), the outlets (15), the nozzles (31) and the sealing member (32) on the skin contact surface (12) in a position whereby they contact the external surface of the skin in use. The microneedles of the penetrative electrode (2) may extend from the skin contact surface (12) such that in use, the penetrative electrode (2) is inserted into the skin of a human or animal body such that the electrical contacts (3) of the tips (13) is positioned beneath the stratum corneum of the human or animal. The delivery system (1) also comprises a housing (7) in the form of a handle enabling a user to hold the system (1) when positioning the skin contact surface (12) on or adjacent to the surface of the skin. The housing (7) includes electrical circuitry (not shown in FIG. 5) such that a potential difference is applied between the surface electrode (4) and the electrical contacts (3) of the penetrative electrode (2) generating an electrical field. For example, the surface electrode (4) may be positively charged and the penetrative electrode (2) may be negatively charged. The nozzles (31) are connected to a source of suction (33) that withdraws air from the nozzles (31) in operation, thus generating a partial vacuum in a suction zone between the skin contact surface (12) and the skin in use. The delivery outlets (15) are part of a dispenser that also includes a reservoir (16) for an active agent to be delivered by the delivery system (1) and an actuator (17) configured to produce a flow of the active agent from the reservoir (16) to the outlets (15). The microneedles of the penetrating electrode (2) are originated such that each individual microneedle penetrates the skin in a direction substantially perpendicular to the stratum corneum in use.

Figure 6:
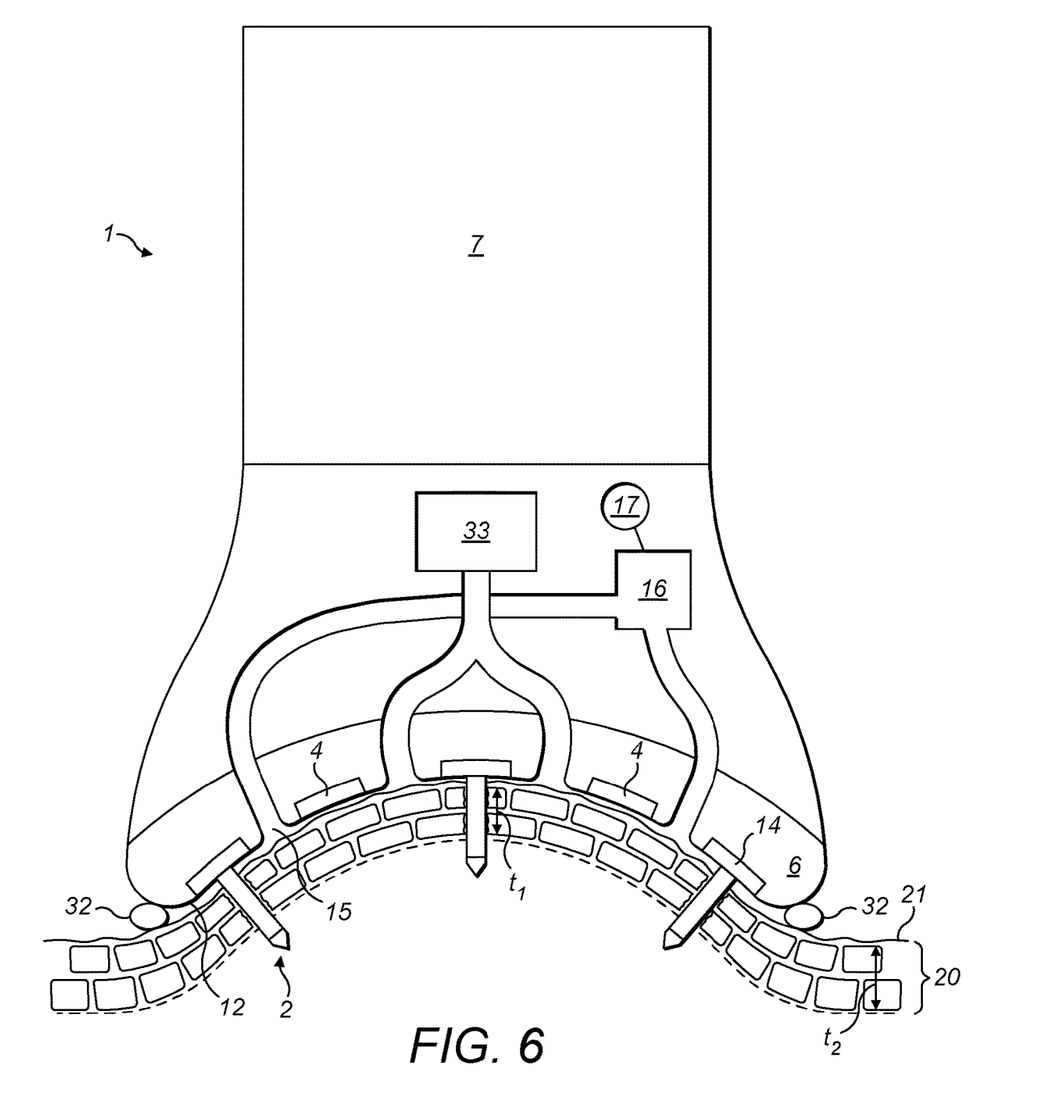
FIG. 6 shows the transdermal delivery system according to the fourth embodiment of the invention in use.

FIG. 6 shows the transdermal delivery system (1) of the fourth embodiment in use. The suction head (30) of the system (1) has been placed against the surface of the skin (21) and suction has been applied from the suction source (33) to the suction nozzles (15) thereby distorting the surface of the skin (21). As the surface of the skin (21) has distorted, the skin has stretched such that the thickness ($t_1$) of the stratum corneum (2) adjacent to the suction head (30) is less than the thickness ($t_2$) of the stratum corneum (20) at positions remote from the suction head (30). The microneedles of the penetrative electrode (2) are angled such that each microneedle has penetrated the stratum corneum (2) in a direction substantially perpendicular to the stratum corneum (2) as the surface of the skin (21) was drawn into contact with the skin contact surface (12) of the suction head (30). The sealing member (32) that forms a perimeter around a suction zone has deformed on contact with the skin surface (21) and forms a tight seal around the suction zone.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

What is claimed is:

1. An electrode assembly for transdermal delivery of an active agent, comprising:
   a penetrative electrode of one polarity configured to provide an electrical contact beneath the stratum corneum;
   a surface electrode of the opposite polarity configured to provide an electrical contact to the external surface of the skin;
   a dispenser configured to dispense the active agent to the external surface of the skin,
   wherein the penetrative electrode includes a plurality of microneedles that project from a skin contact surface and are configured to be inserted into the skin of the human body, the microneedles comprising shafts extending from bases on the skin contact surface to tips, wherein the exterior of the shafts are electrically insulated and the tips provide the electrical contact beneath the stratum corneum.

2. The electrode assembly of claim 1,
   wherein the penetrative electrode and surface electrode are electrically insulated from each other;
   wherein the dispenser includes an outlet at the skin contact surface; and
   wherein the surface electrode is present on the skin contact surface.

3. The electrode assembly of claim 2, wherein the microneedles of the penetrative electrode are at least 10 µm in length.

4. The electrode assembly of claim 2, wherein the maximum length of the microneedles of the penetrative electrode is 200 µm.

5. The electrode assembly of claim 2, wherein an electrically conducting material is present in the interior of the shafts of the microneedles of the penetrative electrode to conduct electricity to the tips.

6. The electrode assembly according to claim 5, wherein the electrically conducting material comprises titanium, gold, or alloys thereof.

7. The electrode assembly according to claim 1, comprising an electrical circuit configured to apply a voltage differential between the electrical contact of the penetrative electrode and an electrical contact of the surface electrode.

8. The electrode assembly of claim 7, wherein the electric circuit is configured to vary the voltage differential between the electrical contact of the penetrative electrode and the electrical contact of the surface electrode.

9. The electrode assembly according to claim 1, wherein the electrode assembly is configured such that, in use, an electric field is generated that is orientated substantially perpendicular to the stratum corneum.

10. The electrode assembly according to claim 1, wherein the electrical contact of the penetrative electrode has an uneven surface.

11. The electrode assembly according to claim 1, further comprising a suction head configured to apply suction to the external surface of the skin.

12. The electrode assembly of claim 11, wherein the suction head is configured to apply suction to a suction zone and within which suction zone the penetrative electrode and surface electrode are mounted.

13. A transdermal delivery system comprising the electrode assembly according to claim 1 and an active agent present in the dispenser.

14. The electrode assembly of claim 2, wherein the microneedles of the penetrative electrode are at least 30 μm in length.

15. The electrode assembly of claim 2, wherein the maximum length of the microneedles of the penetrative electrode is 80 μm.

16. An electrode assembly for transdermal delivery of an active agent, comprising:
a penetrative electrode of one polarity configured to provide an electrical contact beneath the stratum corneum;
a surface electrode of the opposite polarity configured to provide an electrical contact to the external surface of the skin;
a dispenser configured to dispense the active agent to the external surface of the skin;
wherein the penetrative electrode includes a plurality of microneedles that project from a skin contact surface and are configured to be inserted into the skin of the human body, the microneedles comprising shafts extending from bases on the skin contact surface to tips, wherein the exterior of the shafts are electrically insulated and the tips provide the electrical contact beneath the stratum corneum; and wherein the electrode assembly is configured such that, in use, an electric field is generated that is orientated substantially perpendicular to the stratum corneum.

* * * * *